United States Patent [19]

Loosemore et al.

[11] 4,080,574
[45] Mar. 21, 1978

[54] APPARATUS FOR PROVIDING TIME REFERENCE SIGNALS

[75] Inventors: William Ronald Loosemore, Abingdon; Albert Henry Muston, Newbury, both of England

[73] Assignee: United Kingdom Atomic Energy Authority, England

[21] Appl. No.: 688,945

[22] Filed: May 24, 1976

Related U.S. Application Data

[63] Continuation of Ser. No. 543,354, Jan. 23, 1975, abandoned.

[30] Foreign Application Priority Data

Jan. 31, 1974 United Kingdom .................. 4665/74

[51] Int. Cl.$^2$ ............................................... H03K 5/18
[52] U.S. Cl. ...................................... 328/109; 307/232; 307/362; 328/115; 328/147
[58] Field of Search ................ 307/233, 235 E, 235 T, 307/232; 328/135, 136, 146–149, 115, 109, 110

[56] References Cited

U.S. PATENT DOCUMENTS

| | | | |
|---|---|---|---|
| 3,505,537 | 4/1970 | Giordano | 307/235 T |
| 3,559,080 | 1/1971 | Kobori et al. | 328/136 |
| 3,781,692 | 12/1973 | Escoffier | 307/235 T |

*Primary Examiner*—John Zazworsky
*Attorney, Agent, or Firm*—Larson, Taylor and Hinds

[57] ABSTRACT

Apparatus for providing an accurate time reference upon a pulse of high frequency electrical signal oscillations comprises a zero crossover detector which includes an amplitude threshold detector, which signals the next positive going zero-crossover of the signal after the threshold detector has operated. An integrating amplifier provides a measure of the integrated pulse amplitude which indicates whether or not the pulse was of adequate amplitude correctly to operate the zero crossover detector.

4 Claims, 5 Drawing Figures

APPARATUS FOR PROVIDING TIME REFERENCE SIGNALS

This is a continuation, of application Ser. No. 543,354 filed Jan. 23, 1975, and now abandoned.

BACKGROUND OF THE INVENTION

The invention relates to apparatus for providing time reference signals. In particular, the invention is concerned with providing time reference signals from pulses of high frequency electrical signal oscillations such as are used for example in the measurement of fluid flow velocities using ultrasonic pulses.

SUMMARY OF THE INVENTION

The invention provides apparatus for providing a time reference signal from a pulse of electrical signal oscillations, which apparatus comprises a zero crossover detector including detector means for detecting arrival presence of a pulse, for providing a signal output at the moment when the electrical signal oscillation passes through zero subsequently to detection by the said detector means, and indicator means for providing an indication whether or not the amplitude of the detected pulse is adequate for proper operation of the zero crossover detector.

Preferably the indicator means comprises an integrating amplifier connected to receive the said pulse and to provide an output indicative of the integrated amplitude of the oscillating signal over the total duration of the pulse.

The operation of the zero cross-over detector in providing an output coincident with a particular selected zero crossover of the received pulse will only be satisfactory provided the amplitude of the received pulse lies within predetermined limits. Thus the output of the integrating amplifier provides a check to show whether the operation of the zero crossover detector has occurred under satisfactory conditions.

Preferably, comparator means is provided for comparing the output of the integrating amplifier with a reference standard. Usually, the output from the zero crossover detector is fed to other apparatus for performing logic and/or control functions. In that case, it is convenient to provide means responsive to the output from the comparator means for inhibiting operation of such logic and/or control apparatus in the event that comparison of the output of the integrating amplifier with the reference standard indicates conditions in which the operation of the zero crossover detector is likely to be unsatisfactory.

BRIEF DESCRIPTION OF THE DRAWINGS

Specific constructions of apparatus embodying the invention will now be described by way of example and with reference to the drawings filed herewith, in which.

DESCRIPTION OF PREFERRED EMBODIMENT

In this example, the invention is embodied in an equipment for measuring the velocity or a component of velocity of fluid flow as described in the specification of U.S. Pat. No. 3,894,431. The equipment operates on the principle of starting simultaneously the transmission through the fluid of a pulse of ultrasound and the counting of pulses from or oscillations from voltage controlled oscillator. The time of arrival of the received pulse of ultrasound is compared with the time of arrival of the Nth pulse or oscillation from the voltage controlled oscillator and adjustments are made to the frequency of oscillation of the voltage controlled oscillator to tend to bring these respective times of arrival into coincidence. By fitting, in this way, a predetermined number (N) of pulses or oscillations into the time of flight of ultrasonic pulses through the fluid along the same path but in opposite directions, it is possible to compute the component of fluid flow velocity along that path from the difference in frequency of voltage controlled oscillator corresponding to the two opposed directions of transmission of the ultrasonic pulses.

It will be appreciated that the accuracy of the equipment will be dependent, among other things, upon the accuracy with which a time reference may be established upon the received ultrasonic pulse.

Figure 1:
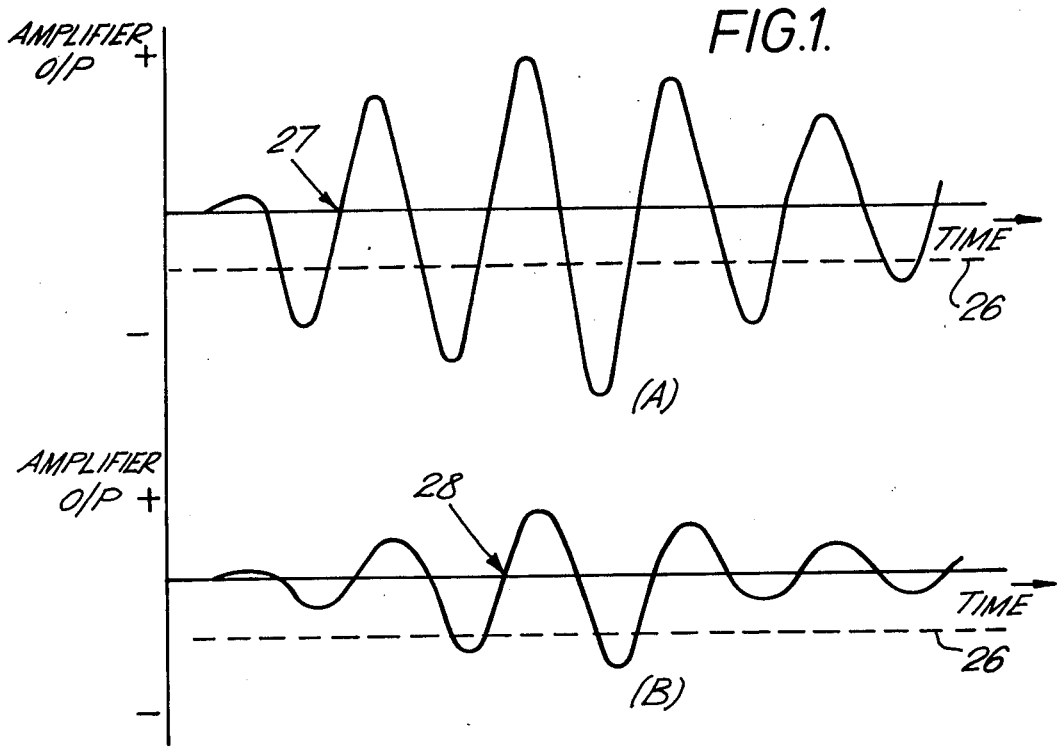
FIG. 1 shows first and second signal wave forms.
Figure 2A:
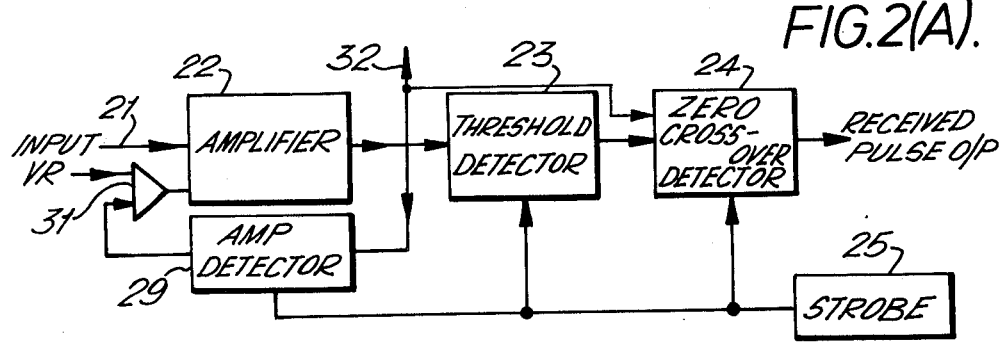
FIGS. 2A and 2B are circuit diagrams of part of the apparatus.

A transducer converts the received ultrasonic pulse into an electrical signal and the waveform of this signal is illustrated in FIG. 1 at (A) and (B) which are graphs in which the abscissa represents time and the ordinate represents signal amplitude at the output from an amplifier 22 (see FIG. 2A).

Referring to FIG. 2A, the signal from the transducer is fed at 21 to the amplifier 22, the output from which is applied to a zero crossover detector. A conventional zero crossover detector incorporates a threshold detector for preventing the zero crossover detector from operating except when it receives signal excursions in excess of a predetermined level. This is a very necessary requirement of a zero crossover detector since otherwise it would be continuously firing on every positive-going zero-crossover of the noise signal that will inevitably be present at its input. This aspect of the operation of a zero crossover detector and the effect of the threshold level at which it is set to operate are important for consideration in the present application and, for convenience of description, the threshold detector and zero crossover detector components of a conventional zero crossover detector are shown separately at 23 and 24, respectively, in FIG. 2A. The operation is controlled by a strobe 25 which makes the detector circuitry live only during a predetermined period embracing the expected time of arrival of a pulse. The purpose of the strobe is to prevent unwanted operation from spurious signals.

In FIG. 1, waveform (A) illustrates a received signal of amplitude sufficient for normal operation. The dotted line 26 represents the threshold level set by the threshold detector 23. The arrangement is that the zero crossover detector provides an output on the next positive going zero crossover of the received signal after a negative going excursion of the signal has exceeded the threshold detector level 26. The zero crossover detector output will thus correspond with the position 27 shown on waveform (A) of FIG. 1.

It will be appreciated that the amplitude of the received ultrasonic pulse may be expected to vary, particularly if there are gas bubbles or solids in suspension in the fluid. The above mentioned patent specification of U.S. Pat. No. 3,894,431 describes how provision may be made to avoid error in the flow measurement indicated by the equipment as a result of complete obstruction of some of the ultrasonic pulses. However, it is possible for the equipment to detect a received signal and to operate but to give an erroneous result because the amplitude of the detected signal is too low. This is illustrated in FIG. 1, waveform (B), in which it can be seen that the received signal has been so attenuated that the first negative going excursion does not operate the threshold detector but the second negative going excursion does operate the threshold detector. The zero crossover detector will then provide and output at position 28 in waveform (B) of FIG. 1 which is displaced by the period of one complete cycle of the high frequency oscillation from the desired position for the time reference.

This effect can be reduced by the provision of automatic gain control for the amplifier 22. This is indicated in FIG. 2A in which a device 29 detects the amplitude of the output from amplifier 22 and provides a voltage signal indicative of this amplitude which is compared with a reference voltage VR by comparator 31. The output from comparator 31 controls the gain of amplifier 22 to tend to maintain the amplitude of the output signal at a constant level.

Figure 2B:
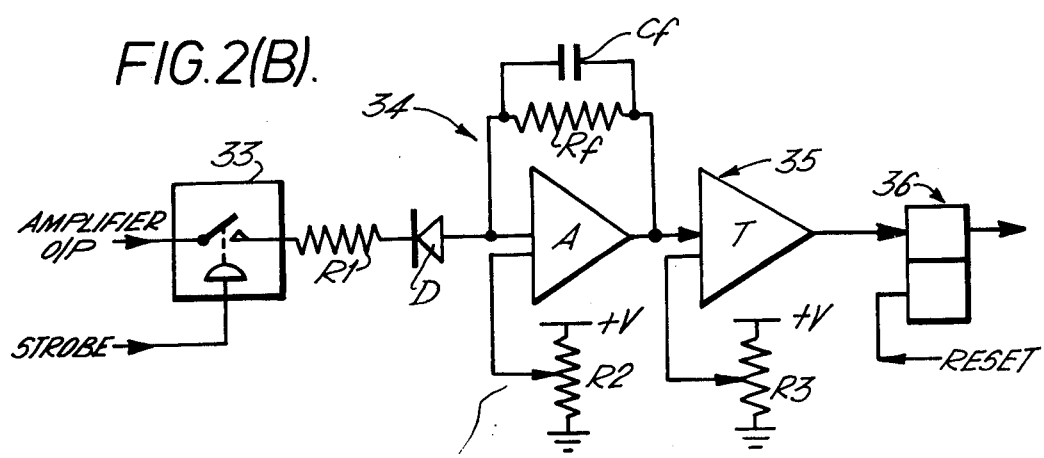

However, the automatic gain control necessarily operates with a relatively long time constant, adjusting the amplifier gain only when the average received signal level changes. It is therefore possible, for example if only a small proportion of severely attenuated signals is received, for such attenuated signals to reach the threshold detector 23 in the form illustrated in FIG. 1B. FIG. 2B illustrates apparatus for providing an output signal to indicate that the amplitude of the received signal fed to threshold detector 23 is satisfactory. The output from amplifier 22 at line 32 is fed via linear gate 33 controlled by the strobe 25 to an integrating amplifier 34. The output from the integrating amplifier 34 is compared with a reference voltage by a trigger circuit 35 which is arranged to set a fli-flop 36 in the event that the output from the integrating amplifier exceeds a predetermined level. The operation of this circuit is as follows.

The linear gate 33 is turned on by the strobe pulse so that the output from amplifier 22 is only connected to the integrating amplifier 34 during the strobe time period, that is the period embracing the expected time of arrival of a received pulse.

The input to the integrating amplifier is low impedance (a "summing" point) at the voltage set by the variable resistor R2. The diode D will conduct when the signal is more negative than this voltage by an amount $V_f$ where $V_f$ is the voltage required for diode D to conduct. The resistor R2 is set so that diode D turns on when the signal voltage is a little more negative than amplifier output noise. This avoids any contribution to the integrating amplifier from this noise.

The time constant of the capacitor resistance combination $C_fR_f$ is arranged to be much greater than the strobe time and much less than the delay between receipt of successive received pulses. In this way true integration can take place during the strobe time but there is ample time for the voltage across capacitor $C_f$ to decay to zero before the next strobe pulse.

The instantaneous current flow through the resistor R1 and diode D into the integrating capacitor $C_f$ is given by:

$$I = \frac{V_{RX} - V_f + V_{R2}}{R_1}$$

where
 $V_{RX}$ = signal amplitude
 $V_f$ = diode forward voltage drop
 $V_{R2}$ = reference voltage to operational amplifier A.

Figure 3:
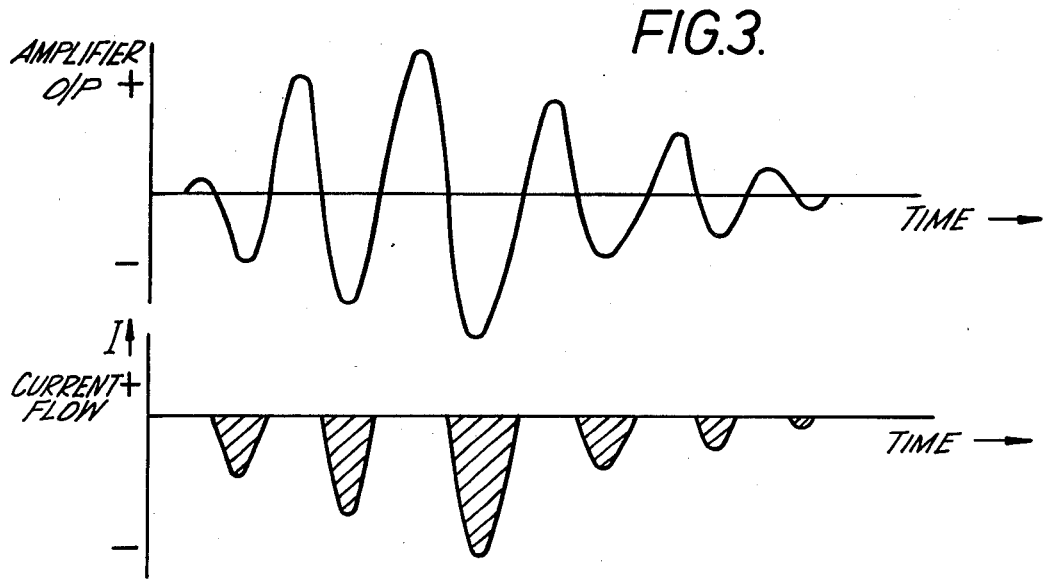
FIG. 3 shows further waveforms.

The form of the current I is shown in the lower part of FIG. 3. The upper part of FIG. 3 shows the wave form of the output from the amplifier 22 for comparison.

The output voltage from the operational amplifier A applied to the trigger circuit 35 will be proportional to the total charge integrated in the capacitor $C_f$ during the strobe time, that is the output voltage will be proportional to the total shaded area in FIG. 3.

The trip level of the trigger circuit 35 is adjusted using variable resistor R3 so that a received signal which has a mean amplitude sufficient to produce a voltage output from the integrating amplifier greater than this trip level will be comfortably large enough to operate the zero crossover detector correctly.

Figure 4:
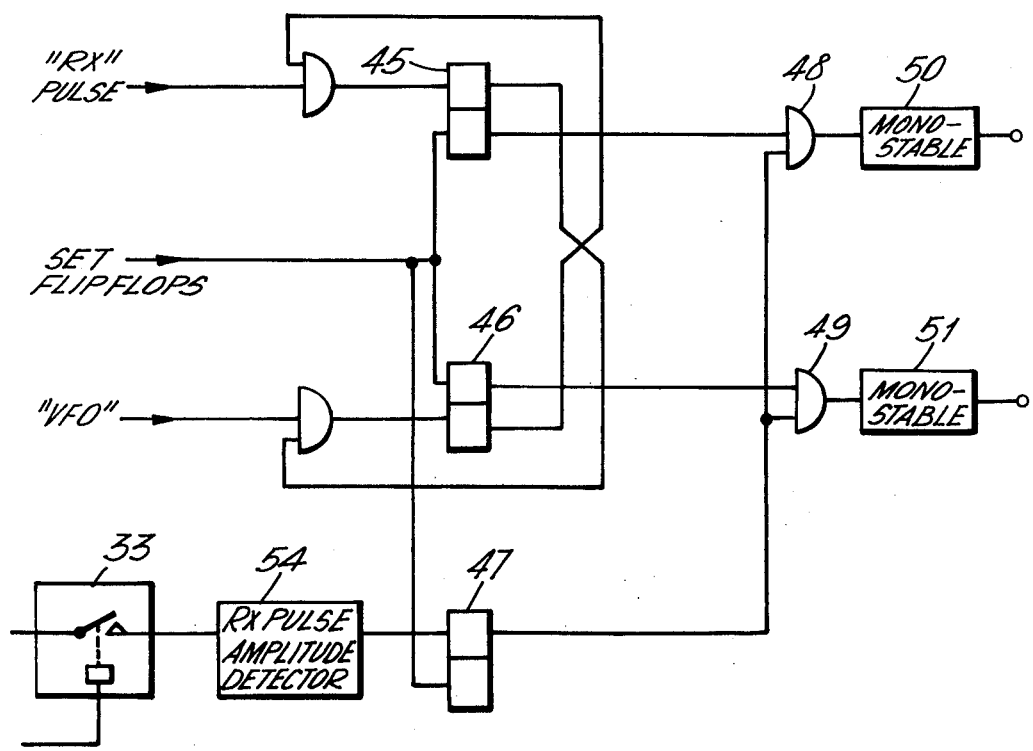
FIG. 4 is a block circuit diagram of part of an apparatus in which the apparatus of FIGS. 2A and 2B is incorporated.

FIG. 4 illustrates how the apparatus of FIGS. 2A and 2B is incorporated into the flow measurement equipment. FIG. 4 shows that portion of the equipment corresponding to FIG. 3 in the specification of U.S. Pat. No. 3,894,431.

The part of the apparatus shown in FIGS. 2A provides an output marked RECEIVED PULSE O/P. As described above, this is a signal pulse in time coincidence with an accurate time reference point upon the input signal at 21, that is, the electrical counterpart of the received ultrasonic signal. This accurate time reference output, denoted RECEIVED PULSE O/P, is connected to the input denoted 'RX' PULSE in FIG. 4.

The FIG. 2B apparatus is incorporated into the flow measurement equipment so as to inhibit adjustment of the voltage controlled oscillators in the event that the received pulse amplitude is too low to operate the zero crossover detector satisfactorily. The operation of the circuit of FIG. 4 is as follows:

A start pulse from the master oscillator (not shown) resets all three flip-flops 45, 46 and 47. Either a received pulse RX or a pulse from the voltage controlled oscillator can set flip-flop 45 or flip-flop 46 according to which pulse arrives first. Thus, if the received RX pulse arrives first flip-flop 45 is set and inhibits subsequent setting of flip-flop 46. If the Nth pulse from the voltage controlled oscillator arrives first, the flip-flop 46 is set first and inhibits subsequent setting of flip-flop 45.

If the received RX pulse arrives first, adjustment of the voltage controlled oscillator frequency is effected by an incremental amount by a monostable circuit 50 which operates a level shift as described in the specification of U.S. Pat. No. 3,894,431. However, an output from the set flip-flop 45 is applied to the monostable 50 via AND gate 48 which inhibits operation of the monostable unless and untill the flip-flop 47 is set.

Similarly, the corresponding reduction in frequency of the voltage controlled oscillator in the event that the Nth pulse from the voltage controlled oscillator arrives first is effected by a monostable circuit 51 and associated level shift. Here again, output from set flip-flop 46 is fed to monostable 51 via AND gate 49 which inhibits operation of the monostable 51 unless and until the flip-flop 47 is set.

Flip-flop 47 corresponds to flip-flop 36 in FIG. 2B and is controlled by the output of the combined integrating amplifier 34 and trigger circuit 35 represented by box 54 in FIG. 4 which, in turn, is supplied with the signal output from the amplifier 22 via strobed linear gate 33. Thus, neither monostable 50 nor monostable 51 is permitted to operate unless a recieved signal has an amplitude judged by the arrangement of FIG. 2B to be sufficient for the zero crossover detector to have operated satisfactorily.

The arrangement of FIG. 4 incorporates naturally the provision for no adjustment in the event of obstruction of the ultrasonic pulse for, in that event, there will be no received pulse and flip-flop 47 will remain in its reset condition.

Provided that a certain minimum proportion (for example 10%) of received signal are normal then the control voltage memory of the voltage controlled oscillator will allow correct operation in a manner which corresponds directly with that described in the patent specification of U.S. Pat. No. 3,894,431 in respect of operation when a proportion of received signals are completely absent.

The invention is not restricted to the details of the foregoing examples. Thus, the apparatus illustrated in FIG. 2B is particularly advantageous when employed in the manner shown in FIG. 4 in the equipment described in the patent specification of U.S. Pat. No. 3,894,431 for fluid flow measurement. However, the apparatus of FIG. 2B may be employed wherever it is desired to establish an accurate time reference upon a signal pulse of the form illustrated in FIG. 1.

We claim:

1. Apparatus for providing an output indicative of which of (i) a received pulse of electrical signal oscillations, and (ii) a reference electrical signal pulse occurs first in time said apparatus comprising a zero crossover detector, including detector means for detecting the arrival presence of the received pulse, for providing an accurate time reference signal output at the moment when the electrical signal oscillation passes through zero subsequently to detection by the said detector means, an integrating amplitude detector and indicator means for providing a control signal output when the amplitude of the said received pulse, as integrated over a predetermined time period, exceeds a predetermined level, adequate for operation of the zero crossover detector, to provide the said accurate time reference signal output, first, second and third bistable devices connected to receive, respectively, the said control signal output, the said reference electrical signal pulse and the said accurate time reference signal output, and to change state in response thereto, first and second output lines and logic circuitry means for interconnecting said bistable devices and said output lines so as to provide an output signal upon said first line in response to the first bistable device changing state and the second bistable device changing state before the third bistable device and an output signal on said second line in response to the first bistable device changing state and the third bistable device changing state before the second bistable device, whereby an output on the said first line indicates that the said reference signal pulse occurred before the said received pulse of electrical signal oscillations, an output on the said second line indicates that the said received pulse of electrical signal oscillations occurred before the said reference signal pulse and no output on either line indicates the absence of received pulses of electrical signal oscillations of amplitude adequate to ensure generation of a said accurate time reference signal output.

2. Apparatus as claimed in claim 1, further comprising means for resetting of the bistable devices after each operation independently of the output states on the said two output lines.

3. Apparatus as claimed in claim 1, wherein strobe means are connected to the apparatus for inhibiting operation of the apparatus except during periods of time embracing expected arrival times of received pulses of electrical signal oscillations.

4. In acoustic pulse equipment for measuring fluid flow, apparatus for providing an output indicative of which of (i) a received pulse of electrical signal oscillations, and (ii) a reference electrical signal pulse, occurs first in time, said apparatus comprising a zero crossover detector, including detector means for detecting arrival presence of the received pulse, for providing an accurate time reference signal output at the moment when the electrical signal oscillation passes through zero subsequently to detection by the said detector means, an integrating amplitude detector and indicator means for providing a control signal output when the amplitude of the said received pulse, as integrated over a predetermined time period, exceeds a predetermined level adequate for operation of the zero crossover detector, the output of the indicator means being connected to one terminal of a first bistable device, the reference signal electrical pulse being applied to one terminal of a second bistable device through a first AND gate, the output of the zero crossover detector being connected to one terminal of a third bistable device through a second AND gate, each bistable device having a second terminal input connected to receive resetting signal pulses, the first bistable device having an output, energized when the first bistable device changes state in response to a control signal output indicating adequate amplitude of received pulses, which output from the first bistable device is applied as an input to third and fourth AND gates, the second and third bistable devices each having first and second outputs, the first output being energized when the bistable device changes state in response to a signal input from its respective first or second AND gates, the first output of the second bistable device being connected to the third AND gate and the first output of the third bistable device being connected to the fourth AND gate, the second output of each of the second and third bistable devices being energized when the bistable device is in its reset condition, the second output of the second bistable device being connected to the said second AND gate, the second output of the third bistable device being connected to the said first AND gate, whereby an output is provided by the third AND gate when the output from the first bistable device is energized and the first output of the second bistable device is energized prior to the first output of the third bistable device being energized, an output is provided by the fourth AND gate when the output from the first bistable device is energized and the first output of the third bistable device is energized prior to the first output of the the second bistable device being energized, and whereby once one of the second or third bistable devices has changed its state the other is inhibited from subsequently changing its state until after all the bistable devices have been reset.

* * * * *